United States Patent
Groberman et al.

(10) Patent No.: US 10,987,187 B2
(45) Date of Patent: Apr. 27, 2021

(54) MOVEABLE MEDICAL DEVICE CONFIGURED TO OPERATE ONLY WITHIN A SPECIFIC RANGE OF ACCELERATION

(71) Applicant: Hera Med Ltd., Netanya (IL)

(72) Inventors: David Groberman, Even-Yehuda (IL); Tal Slonim, Rishon Lezion (IL); Shimon Hayun, Rosh Haayin (IL); Joel Rotem, Kfar-Sirkin (IL); Michael Nenner, Tel-Aviv (IL)

(73) Assignee: Hera Med Ltd., Netanya (IL)

( * ) Notice: Subject to any disclaimer, the term of this patent is extended or adjusted under 35 U.S.C. 154(b) by 445 days.

(21) Appl. No.: 15/036,860

(22) PCT Filed: Nov. 10, 2014

(86) PCT No.: PCT/IL2014/050977
§ 371 (c)(1),
(2) Date: May 16, 2016

(87) PCT Pub. No.: WO2015/071897
PCT Pub. Date: May 21, 2015

(65) Prior Publication Data
US 2016/0270872 A1 Sep. 22, 2016

Related U.S. Application Data

(60) Provisional application No. 61/903,975, filed on Nov. 14, 2013.

(51) Int. Cl.
*A61B 8/02* (2006.01)
*A61B 8/08* (2006.01)
(Continued)

(52) U.S. Cl.
CPC ............... *A61B 90/03* (2016.02); *A61B 8/02* (2013.01); *A61B 8/0866* (2013.01);
(Continued)

(58) Field of Classification Search
CPC ............ A61B 90/03; A61B 34/25; A61B 8/02
See application file for complete search history.

(56) References Cited

U.S. PATENT DOCUMENTS

| | | | |
|---|---|---|---|
| 6,183,426 B1* | 2/2001 | Akisada | A61B 5/6843 310/316.01 |
| 2001/0014780 A1* | 8/2001 | Martin | A61B 17/22004 601/2 |

(Continued)

FOREIGN PATENT DOCUMENTS

| | | |
|---|---|---|
| CN | 101652101 | 2/2010 |
| CN | 102469957 | 5/2012 |

(Continued)

OTHER PUBLICATIONS

American Institute of Ultrasound in Medicine, AIUM Statement on Measurement of Fetal Heart Rate, Nov. 17, 2011 (Year: 2011).*

(Continued)

*Primary Examiner* — Katherine L Fernandez
*Assistant Examiner* — Colin T. Sakamoto
(74) *Attorney, Agent, or Firm* — Pearl Cohen Zedek Latzer Baratz LLP (57) ABSTRACT

The present invention generally relates to a medical device including a movable instrument (MI) which is activated only when its movement is within an optimal range of acceleration. More particularly the invention relates to a fetal heart rate monitor (FHRM) having a movable Doppler transducer which transceives ultrasound energy only when found within a certain optimal range of acceleration.

9 Claims, 3 Drawing Sheets

(51) Int. Cl.
   *A61B 90/00* (2016.01)
   *A61C 19/04* (2006.01)
   *A61B 34/00* (2016.01)
   *A61B 8/00* (2006.01)
   *A61B 5/024* (2006.01)
   *A61B 17/00* (2006.01)

(52) U.S. Cl.
   CPC ............ *A61B 8/4254* (2013.01); *A61B 8/488* (2013.01); *A61B 8/54* (2013.01); *A61B 34/25* (2016.02); *A61C 19/04* (2013.01); *A61B 5/02416* (2013.01); *A61B 8/429* (2013.01); *A61B 8/4444* (2013.01); *A61B 8/58* (2013.01); *A61B 2017/00075* (2013.01); *A61B 2560/0223* (2013.01); *A61B 2562/0219* (2013.01)

(56) References Cited

U.S. PATENT DOCUMENTS

| | | | |
|---|---|---|---|
| 2001/0034501 A1* | 10/2001 | Tom | A61B 17/3207 604/67 |
| 2004/0230262 A1 | 11/2004 | Sartor et al. | |
| 2005/0154380 A1 | 7/2005 | DeBenedictis et al. | |
| 2007/0032749 A1* | 2/2007 | Overall | A61B 5/02444 600/595 |
| 2007/0038088 A1 | 2/2007 | Rich et al. | |
| 2008/0232604 A1 | 9/2008 | Dufresne et al. | |
| 2010/0160786 A1 | 6/2010 | Nordgren et al. | |
| 2010/0274145 A1* | 10/2010 | Tupin, Jr. | A61B 5/7278 600/511 |
| 2011/0092820 A1 | 4/2011 | Hyeon | |
| 2011/0152688 A1 | 6/2011 | Venugopalan | |
| 2011/0245708 A1* | 10/2011 | Finkel | A61B 5/0484 600/544 |
| 2012/0123226 A1 | 5/2012 | Schwenk et al. | |
| 2012/0232398 A1 | 9/2012 | Roham et al. | |
| 2013/0053697 A1* | 2/2013 | Holl | A61B 8/54 600/459 |
| 2015/0342528 A1* | 12/2015 | Sudo | A61B 5/6843 600/393 |

FOREIGN PATENT DOCUMENTS

| | | |
|---|---|---|
| CN | 202236918 | 5/2012 |
| CN | 102885639 | 1/2013 |
| CN | 102949209 | 3/2013 |
| EP | 1005287 | 6/2000 |
| WO | WO2013/031168 | 3/2013 |

OTHER PUBLICATIONS

International search report for PCT application No. PCT/IL2014/050977 dated Mar. 10, 2015.
European Search Report for Application No. EP14861493.6 dated Jul. 14, 2017.
Chinese Office Action for Application No. 201480072996.5, dated Apr. 11, 2018.
Chinese Office Action for Application No. 201480072996.5, dated May 17, 2019.

* cited by examiner

MOVEABLE MEDICAL DEVICE CONFIGURED TO OPERATE ONLY WITHIN A SPECIFIC RANGE OF ACCELERATION

CROSS-REFERENCE TO RELATED APPLICATIONS

This application is a National Phase of International Patent Application No. PCT/IL2014/050977, filed Nov. 10, 2014, claiming priority from U.S. Provisional Patent Application No. 61/903,975, filed Nov. 14, 2013, which is hereby incorporated by reference.

FIELD OF THE INVENTION

The present invention generally relates to a medical device including a movable instrument (MI) which is activated only when its movement is within an optimal range of acceleration. More particularly the invention relates to a fetal heart rate monitor (FHRM) having a movable Doppler transducer which transceiver ultrasound energy only when found within a certain optimal range of acceleration.

BACKGROUND

Many proactive medical devices utilize functions that maybe hazardous if operating them while they are still in transit to their site of action. For example, a dental drill may injure the oral cavity if accidently activated while in motion towards the teeth. Other medical devices utilize different forms of energy (X-ray, IR, RF and ultrasound) for treatment or diagnostics that over a certain amount of energy transmittance may be harmful. In many applications, it is pointless and possibly even harmful to keep the energy transmission activated while moving the device towards the target.

For example, ultrasound (US) radiation is not harmful in small doses but over a certain amount may be accounted as unsafe. When US radiation penetrates the body, it causes certain elevation in temperature in the contact area and can also produce small pockets of gas in body fluids or tissues, which their effect has not yet been established. These two effects raise particular concern in the contest of pregnancy in which the fetus is exposed to US radiation and are the reason that national and international organizations have advocated prudent use of US Doppler and imaging for pregnancy monitoring. Furthermore, the use of diagnostic US for non-medical purposes such as fetal keepsake videos has been discouraged by these organizations. To date, when a physician uses a fetal heart rate monitor (FHRM) for acquiring a fetal heartbeat signal the Doppler transducer continues to transmit US energy all through the examination. However, when the physician is conducting a search for the location of fetal heartbeat, if the transducer is moving above a certain velocity there is no chance of acquiring a signal and therefore, keeping the Doppler transducer on is useless as well as adding to the accumulation of radiation in the body of the pregnant woman and her fetus. Furthermore, in relatively long monitoring procedures, such as NST, the US Doppler sensor unit is attached to the pregnant woman by means of a belt/harness and the monitoring process stretches up to 60 minutes. During this period it is common the pregnant woman moves, sometimes quite vigorously, and even stands-up and walk. In most cases fetal heart rate readings at these moments are not accurate or even do not exist, therefore there is no point continuing the monitoring process and the delivery of the energy transmission until these excessive movements are back to normal.

Thus, there is a long felt need for a function within a medical device that will enable its operation only when it reached its site of action in the purpose of reducing hazardous outcomes like injuries and introduction of unnecessary amounts of energy.

SUMMARY

The present invention provides a medical device (MD) (100) comprising at least one movable instrument (MI) having an active and an inactive configuration (110); MI is operably coupled to at least one accelerometer (120); wherein MI is in active configuration when the acceleration measured by at least one accelerometer is within a predetermined optimal range of acceleration in situ and in inactive configuration when acceleration is greater or lower than optimal range.

It is another object of the current invention to disclose the MD as defined in any of the above, wherein MI is proactive; proactive MI is selected from a group consisting of: energy emitting probes, surgical tools, dental tools and any combination thereof.

It is another object of the current invention to disclose the MD as defined in any of the above, wherein predetermined optimal range comprises a lower essential human movement threshold and a predetermined proactive upper movement threshold.

It is another object of the current invention to disclose the MD as defined in any of the above, wherein MD additionally comprises a feature for inserting input regarding parameters of the patient selected from a group consisting of: posture, age, illness, mental status, gender, age and any combination thereof parameters are considered when setting lower essential human movement threshold.

It is another object of the current invention to disclose the MD as defined in any of the above, wherein feature is selected from a group consisting of: (a) at least one button; (b) multiple choice touch screen; (c) a keyboard; (d) a movable scale; (e) at least one switch; and any combination thereof.

It is another object of the current invention to disclose the MD as defined in any of the above, additionally comprising calibrating means useful for accommodating a specific lower essential human movement threshold for a specific person.

It is another object of the current invention to disclose the MD as defined in any of the above, wherein MD is adapted for diagnostics or treatment.

It is another object of the current invention to disclose the MD as defined in any of the above, wherein MD comprises a processor having an input module for receiving acceleration from accelerometer and directions thereon for determining whether acceleration is within predetermined optimal range according to n measurements taken in a certain period of time.

It is another object of the current invention to disclose the MD as defined in any of the above, wherein MD includes means of transportation.

It is another object of the current invention to disclose the MD as defined in any of the above, wherein MI is operably coupled to at least one pressure sensing module; MI is adapted to be in active configuration when the pressure measured by at least one pressure sensing module is above a predetermined threshold.

It is another object of the current invention to disclose the MD as defined in any of the above, wherein MI is operably coupled to at least one photoplethysmograph (PPG); MI is in active configuration when the density of red blood cells measured by PPG is above a certain threshold.

It is another object of the current invention to disclose the MD as defined in any of the above, wherein MD is adapted to be powered by batteries.

It is another object of the current invention to disclose the MD as defined in any of the above, wherein all functions of MD, excluding accelerometer, are in an inactivate configuration when acceleration is below lower essential human movement threshold.

It is another object of the current invention to disclose the MD as defined in any of the above, additionally comprising a manual activator for activating movable instrument; instrument operates only when instrument is within optimal range and manual activator is activated It is another object of the current invention to disclose the MD as defined in any of the above, wherein MD comprises solely of MI.

It is another object of the current invention to disclose the MD as defined in any of the above, wherein MI is connected to MD in a manner selected from a group consisting of physically, wirelessly and any combination thereof.

It is another object of the current invention to disclose the MD as defined in any of the above, wherein the MI has affixing means adapted to affix the MI to said patient for a period of time without being held.

It is another object of the current invention to disclose a method for increasing safety of a medical device (MD) comprising at least one movable instrument (MI) having an active and an inactive configuration, comprising steps of: (a) obtaining MD, comprising at least one MI; (b) operably coupling at least one accelerometer to MI; and, (c) operating MD; wherein at least one MI is in an activate configuration when the acceleration measured by at least one accelerometer is within a predetermined optimal range of acceleration in situ and an inactive configuration when acceleration is greater or lower than optimal range.

It is another object of the current invention to disclose the method as defined in any of the above, additionally comprising a step f selecting MI from a group of proactive instruments consisting of: energy emitting probes, surgical tools, dental tools and any combination thereof.

It is another object of the current invention to disclose the method as defined in any of the above, additionally comprising a step of determining predetermined optimal range according to a lower essential human movement threshold and a predetermined proactive upper movement threshold.

It is another object of the current invention to disclose the method as defined in any of the above, additionally comprising steps of: (a) inserting through a feature input regarding parameters of the patient selected from a group consisting of posture, age, illness, mental status, gender, age and any combination thereof and (b) considering parameters when setting lower essential human movement threshold.

It is another object of the current invention to disclose the method as defined in any of the above, additionally comprising a step of selecting a feature for inserting input from a group consisting of: (a) at least one button; (b) multiple choice touch screen; (c) a keyboard; (d) a movable scale; (e) at least one switch; and any combination thereof.

It is another object of the current invention to disclose the method as defined in any of the above, additionally comprising a step of accommodating lower essential human movement threshold according to the specific essential human movement of a specific person.

It is another object of the current invention to disclose the method as defined in any of the above, wherein using method for diagnosing and for treating patients.

It is another object of the current invention to disclose the method as defined in any of the above, additionally comprising a step of attaching a processor to MD; processor is receiving acceleration and has directions thereon for determining whether acceleration is within predetermined optimal range according to n measurements taken in a certain period of time.

It is another object of the current invention to disclose the method as defined in any of the above, additionally comprising a step of mobilizing MD.

It is another object of the current invention to disclose the method as defined in any of the above, additionally comprising a step of operably coupling to MI at least one pressure sensing module; at least one MI is in an active configuration when the pressure measured by at least one pressure sensing module is above a predetermined threshold.

It is another object of the current invention to disclose the method as defined in any of the above, additionally comprising a step of operably coupling to MI to at least one photoplethysmograph (PPG);

It is another object of the current invention to disclose the method as defined in any of the above, additionally comprising a step of powering MD by batteries.

It is another object of the current invention to disclose the method as defined in any of the above, additionally comprising a step of deactivating all functions of MD, excluding accelerometer, when acceleration is below lower essential human movement threshold.

It is another object of the current invention to disclose the method as defined in any of the above, additionally comprising a step of activating a manual activator for activating movable instrument.

It is another object of the current invention to disclose the method as defined in any of the above, additionally comprises a step of connecting MI to MD in a manner selected from a group consisting of physically, wirelessly and any combination thereof.

It is another object of the current invention to disclose the method as defined in any of the above, additionally comprises a step of affixing the MI to the patient without holding it for a period of time.

It is another object of the current invention to disclose a fetal heart rate monitor (FHRM) (100) comprising at least one movable Doppler transducer (110) having a transceiving configuration and an inactive configuration; at least one movable Doppler transducer is operably coupled to at least one accelerometer (120); wherein at least one movable Doppler transducer is in transceiving configuration when the acceleration measured by at least one accelerometer is within a predetermined optimal range of acceleration in situ and in inactive configuration when acceleration is greater or lower than optimal range.

It is another object of the current invention to disclose the FHRM as defined in any of the above, wherein optimal range comprises a lower essential human movement threshold and a predetermined proactive upper movement threshold.

It is another object of the current invention to disclose the FHRM as defined in any of the above, wherein FHRM additionally comprises a feature for inserting input regarding parameters of the patient selected from a group consisting of posture, age, illness, mental status, gender, age and any combination thereof; parameters are used to determine lower essential human movement threshold.

It is another object of the current invention to disclose the FHRM as defined in any of the above, wherein feature is selected from a group consisting of: (a) at least one button; (b) multiple choice touch screen; (c) a keyboard; (d) a movable scale; (e) at least one switch; and any combination thereof.

It is another object of the current invention to disclose the FHRM as defined in any of the above, additionally comprising calibrating means useful for accommodating a specific lower essential human movement threshold for a specific person.

It is another object of the current invention to disclose the FHRM as defined in any of the above, wherein FHRM comprises a processor having an input module for receiving acceleration from accelerometer and directions thereon for determining whether acceleration is within predetermined optimal range according to n measurements taken in a certain period of time.

It is another object of the current invention to disclose the FHRM as defined in any of the above, wherein FHRM includes means of transportation.

It is another object of the current invention to disclose the FHRM as defined in any of the above, wherein at least one movable Doppler transducer is comprised of at least one Piezoelectric ceramic element.

It is another object of the current invention to disclose the FHRM as defined in any of the above, wherein at least one movable Doppler transducer is operably coupled to at least one pressure sensing module; at least one movable Doppler transducer is adapted to be in transceiving configuration when the pressure measured by at least one pressure sensing module is above a predetermined threshold.

It is another object of the current invention to disclose the FHRM as defined in any of the above, wherein at least one pressure sensing module is at least one Piezoelectric ceramic element.

It is another object of the current invention to disclose the FHRM as defined in any of the above, wherein at least one movable Doppler transducer is operably coupled to at least one photoplethysmograph (PPG); at least one movable Doppler transducer is in transceiving configuration when the density of red blood cells measured by PPG is above a certain threshold.

It is another object of the current invention to disclose the FHRM as defined in any of the above, wherein FHRM is adapted to be powered by batteries.

It is another object of the current invention to disclose the FHRM as defined in any of the above, wherein all functions of FHRM, excluding accelerometer, are adapted to be deactivated when acceleration is below lower essential human movement threshold.

It is another object of the current invention to disclose the FHRM as defined in any of the above, additionally comprising a manual activator for activating at least one movable Doppler transducer; at least one movable Doppler transducer operates only when at least one movable Doppler transducer is within optimal range and manual activator is activated.

It is another object of the current invention to disclose the FHRM as defined in any of the above, wherein at least one movable Doppler transducer has affixing means adapted to affix at least one movable Doppler transducer to the patient for a period of time without being held.

It is another object of the current invention to disclose a method for increasing safety of a fetal heart rate monitor (FHRM) comprising at least one movable Doppler transducer having an transceiving configuration and an inactive configuration, comprising steps of; (a) obtaining FHRM, comprising at least one movable Doppler transducer; (b) operably coupling an accelerometer to at least one movable Doppler transducer; and, (c) operating FHRM; wherein at least one movable Doppler is in transceiving configuration when the acceleration measured by at least one accelerometer is within a predetermined optimal range of acceleration in situ and an inactive configuration when acceleration is greater or lower than optimal range.

The method additionally comprising a step of determining optimal range by a lower essential human movement threshold and a predetermined proactive upper movement threshold.

It is another object of the current invention to disclose the method as defined in any of the above, additionally comprising steps of: (a) inserting through a feature input regarding parameters of the patient selected from a group consisting of posture, age, illness, mental status, gender, age and any combination thereof; and (b) considering parameters when setting lower essential human movement threshold.

It is another object of the current invention to disclose the method as defined in any of the above, additionally comprising a step of selecting a feature for inserting input from a group consisting of: (a) at least one button; (b) multiple choice touch screen; (c) a keyboard; (d) a movable scale; (e) at least one switch; and any combination thereof.

It is another object of the current invention to disclose the method as defined in any of the above, additionally comprising a step of accommodating lower essential human movement threshold according to the specific essential human movement of a specific person.

It is another object of the current invention to disclose the method as defined in any of the above, additionally comprising a step of attaching a processor to FHRM; processor is receiving acceleration and has directions thereon for determining whether acceleration is within predetermined optimal range according to n measurements taken in a certain period of time.

It is another object of the current invention to disclose the method as defined in any of the above, additionally comprising a step of mobilizing FHRM.

It is another object of the current invention to disclose the method as defined in any of the above, additionally comprising a step of operably coupling to at least one Doppler transducer to at least one pressure sensing module; at least one Doppler transducer is in transceiving configuration when the pressure measured by at least one pressure sensing module is above a predetermined threshold.

It is another object of the current invention to disclose the method as defined in any of the above, additionally comprising a step of operably coupling to at least Doppler transducer to at least one photoplethysmograph (PPG); at least one Doppler transducer is in transceiving configuration when the density of red blood cells measured by sad PPG is above a predetermined threshold.

It is another object of the current invention to disclose the method as defined in any of the above, additionally comprising a step of powering FHRM by batteries.

It is another object of the current invention to disclose the method as defined in any of the above, additionally comprising a step of deactivating all functions of FHRM, excluding accelerometer, when acceleration is below lower essential human movement threshold.

It is another object of the current invention to disclose the method as defined in any of the above, additionally comprising a step of activating a manual activator for activating movable instrument.

It is another object of the current invention to disclose the method as defined in any of the above, additionally comprises a step of affixing at least one movable Doppler transducer to the patient without holding it for a period of time.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. The present invention provides a medical device comprising a movable instrument which is activated only when its movement is within a certain optimal range.

In the accompanying drawings.

DETAILED DESCRIPTION OF THE INVENTION

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a medical device (MD), which has a movable instrument (MI) operably coupled to an accelerometer. The accelerometer measures the acceleration of the MI, which may be activated only when the acceleration is within an optimal range. This restriction prevents the instrument from operating while in movement which may cause injury and/or other damage either to the user or to the patient.

The essence of the invention is also to provide a fetal heart rate monitor (FHRM) with a Doppler transducer operably coupled to an accelerometer. Similar to the MI, the transducer transceives only when its acceleration is within the optimal range, thereby preventing it from emitting harmful ultrasound (US) energy into the patient when there is no chance of receiving a meaningful signal. Since the Doppler transducer transmits signals of movements (movements of the heart valves or artery blood flow in this case) any other movement will clearly hamper attempts to receive the heart movement signals. Therefore, an upper movement threshold is determined that above it the heart valve signals will be negligible and it would not be possible to detect them.

To date, several MDs combined with an accelerometer exist, however, for different purposes. For example, patent publication number US2008/0294022 recites a birthing medical monitor in which an accelerometer is used for detecting maternal physiological parameters such as contraction or breathing.

Another example may be found in patent publication number WO2008153999, which recites a thermal surgery safety apparatus that includes a hand piece that comprises a thermistor and an accelerometer. The thermistor is programmed to take temperature measurements only when the accelerometer indicates that the handpiece is moving sufficiently slowly to allow an accurate measurement.

In the present invention, it is acknowledged that many MDs containing a movable instrument are potentially hazardous when been moved towards or away from the target area or when moved to find the target position. For example, a dental drill often causes injuries to the tongue or to the inside of the cheek and gums while the dentist is moving it towards the target tooth. Another example is a fetal heart rate monitor (FHRM) having a movable Doppler transducer which emits radiation unnecessarily and proactively as the instrument is being manipulated into position, with no useful signal being received, therefore endangering the fetus and/or the mother. In the current invention, differently from previous inventions, the instrument is set to operate only when within a specific range of acceleration. It would not operate in an acceleration below a the specific range, which means that the medical device is not held by the operator and/or is not placed on the patient's body and therefore, its use will be dangerous for the surroundings, it will waste battery life (in case the device operates on batteries) without carrying out its function. The device will also not operate in an acceleration above the specific range, which means that it is been moved and not placed steadily in its site of action and therefore, may be hazardous.

The term "in situ" refers hereinafter to a position of a medical device in which it is taking its action with relatively no movement of its movable part. For example, when a Doppler transducer is in an in situ position it means that it is positioned on the body and it is transceiving ultrasound waves without moving it around. The only movement of a medical device in an in situ position results from normal essential human movements of the user of the medical device and the patient on which the device is used.

The term "movable instrument (MI)" refers hereinafter to any instrument of a medical device that has to be moved in order to use it. It may be moved from its base towards the patient or it may be moved along or around the patient's body in order to acquire a signal or reach the site of action. The MI may comprise the whole MD or mat be a part of it.

The term "proactive movable instrument" refers hereinafter to any MI of an MD that has an effect on the body it comes in contact with. The proactive MI may cause long- or short-term damage to the human body upon its activation or no damage at all. More specifically the term refers to any MI that may injure the body (such as drills, polishing instruments, knives, saws, stitching instruments, lasers, etc.) or instruments that transmit radiation (UV, US, X-ray, gamma-ray, particle radiation, ionizing radiation) to the body which introduces energy into the body. In many cases the proactive MI may be hazardous.

Unlike proactive MIs, sensors do not exert an effect on the human body but rather only takes measurements of parameters (for example thermometer, sphygmomanometer, etc.) and are not hazardous under any condition.

The term "energy emitting probes" refers hereinafter to any probe introducing energy within the human body. More specifically the term relates to probes emitting US, X-ray, gamma-ray, particle radiation, ionizing radiation, etc.

The term "surgical tools" refers hereinafter to any tool used during surgery having an effect on the human body. More specifically the term relates to mechanical cutters, lasers, suction, sealing devices, staples, etc.

The term "dental tools" refers hereinafter to any tool used during dental treatment having an effect on the human body. More specifically the term relates to drills, burs, suction, etc.

The term "accelerometer" refers hereinafter to a device that measures proper acceleration. More generally the term refers to bulk micromachined capacitive, bulk micromachined piezoelectric resistive, capacitive spring mass base, DC response, electromechanical servo (Servo Force Balance), high gravity, high temperature, laser accelerometer, low frequency, magnetic induction, modally tuned impact hammers, null-balance, optical, pendulous integrating gyroscopic accelerometer (PIGA), piezoelectric accelerometer, resonance, seat pad accelerometers, shear mode accelerometer, strain gauge, surface acoustic wave (SAW), surface micromachined capacitive (MEMS), thermal (submicrometre CMOS process), triaxial, vacuum diode with flexible anode.

The term "optimal range of acceleration" refers hereinafter to the range of acceleration of a MI resulting solely from essential human movements of the user and/or the patient. The optimal range comprises a lower essential human movement threshold and a predetermined proactive upper movement threshold. Any acceleration above the upper threshold of the optimal range means that the MI is been actively moved which may result in a hazardous event and/or unnecessary introduction of energy and/or radiation into the body. Acceleration above the upper threshold may also mean that the user is making movements above the essential human movements (walking, jumping, etc) and the MI receives the acceleration of the user (mainly in cases in which it is attached to the user for a period of time). Any acceleration below the lower threshold of the optimal range means the instrument is not in use and therefore there is no point in activating it. For example, it is powered up, but not yet being used by the physician or technician on the body of the patient.

The term "essential human movement" refers hereinafter to the base line movement of a living body comprising mainly breathing movements and other involuntarily movements. More specifically the term relates to the essential human movement of the user of a medical device or to the patient the medical device is being used on.

The term "specific lower essential human movement threshold" refers hereinafter to the precise essential human movement characteristic of a certain person used to determine the lower threshold of the optimal range. The essential human movement can also be specific to a certain person in a specific position (lying, sitting standing). The specific lower essential human movement threshold is usually calibrated by the essential human movement of the user of a medical device and/or the patient the medical device is being used on.

The term "proactive upper movement threshold" refers hereinafter to any movement above the essential human movement. If the user of the medical device or the patient it is used on makes voluntary moves or any other moves that are above the threshold the device will cease to operate.

The term "calibrating means" refers hereinafter to means for determining the specific lower essential human movement threshold of a person. These means may also determine the specific essential human movement threshold of a certain person in a specific position (lying, sitting, standing, kneeling, etc.). The calibrating means include the accelerometer measuring the essential human movement of a person and an algorithm determining the threshold according to this measurement. The calibration is usually done according to the user of a medical device and/or the patient the medical device is being used on.

The term "pressure sensing module" refers hereinafter to a module that generates a signal as a function of the pressure imposed. For example, the pressure sensing module can be an absolute pressure sensor, gauge pressure sensor, vacuum pressure sensor, differential pressure sensor, sealed pressure sensor. In some of the embodiments the pressure sensor can be the Piezoelectric ceramic element used for transceiving ultrasonic waves for detecting the FHB signal. The Piezoelectric ceramic element detects pressure by changes in its electric capacity as a result of said pressure; the electric capacity increases as the pressure increases.

The term "photoplethysmograph (PPG)" refers hereinafter to a device used to optically obtain a volumetric measurement of an organ. More specifically the term relates to a simple and low-cost optical technique that can be used to detect blood volume changes in the microvascular bed of tissue. The PPG may be used for determining the density of red blood cells. When a PPG is operably coupled to a MI it can give an indication whether the MI is place on a living object (having red blood cells).

The term "fetal heart rate monitor (FHRM)" refers hereinafter to a device used to detect the heartbeat of a fetus for prenatal care. It is comprised of at least a Doppler transducer, a wave generating module, a communicating module, a processor and other auxiliary electronics.

The term "Doppler transducer" refers hereinafter to the module in the FHRM that utilizes the Doppler effect to convert the movement of the fetus's heart into sound waves.

The term "Piezoelectric ceramic element" refers hereinafter to an element that uses the Piezoelectric effect to measure pressure, acceleration, strain or force by converting them to an electrical charge. The Piezoelectric ceramic element is a transceiver of ultrasonic waves by its microscopic vibrations which are useful for detecting FHB signals by measuring the change in the frequency of the reflecting waves. The Piezoelectric ceramic element is also useful for measuring pressure as its electric capacity increases when pressure increases.

The term "manual activator" refers hereinafter to any switch, trigger or button that has to be activated in order to put the proactive instrument or Doppler transducer in its active or transceiving configuration. This is an additional safety measurement above the activation according to acceleration presented in one of the embodiments of the invention.

The term "means of transportation" refers hereinafter to any means for moving the incubator from one place to another. More specifically the term relates to a cart, trolley, wagon, handcart, pushcart, electric cart, etc.

The term "all functions" refers hereinafter to all function of a medical device or an FHRM like a screen, a processor, audio features, input features, output features, detectors, sensors, lights, etc. According to one embodiment of the invention when the acceleration is below the lower human movement threshold all functions, excluding the accelerometer, are inactivated. Acceleration below the lower threshold is an indication that the medical device or FHRM are not in use and therefore all functions are inactivated for energy saving reasons. The accelerometer is activated in all times in order to be able to sense change in acceleration which will activate all functions when the medical device or FHRM are in use.

The term "period of time" refers hereinafter to any period of time from few seconds to minutes, hours, days and weeks.

The term "affixing means" refers hereinafter to any means that can be used to attached the MI to the body of the patient. More specifically, the term relates to straps, belts, stickers, knots, etc.

The term "affix" refers hereinafter to attaching the MI of an MD to the body of the patient so it does not have to be hand held. In the case of an affixed medical device it has the acceleration of the body it is attached to and there is no movement whatsoever between the sensor and the body. For example, attaching the Doppler transducer for to the abdomen of a pregnant women in order to follow the fetus's heartbeat over a period of time. In another example, EKG electrodes are affixed to the chest of a patient.

Figure 1:
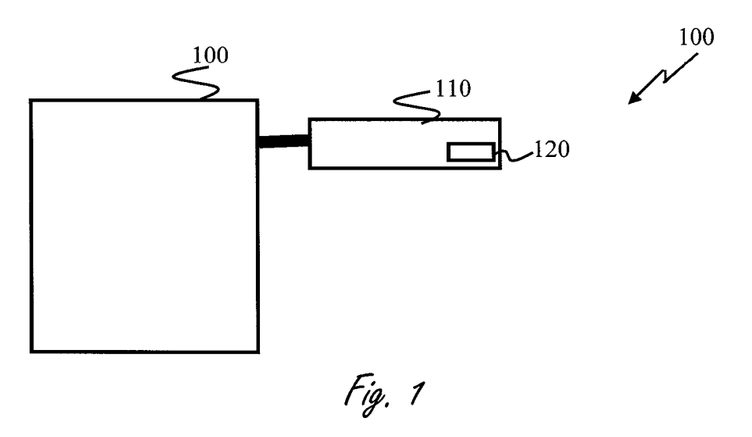
FIG. 1 is a block diagram of a medical device containing a movable instrument (MI)(100)

Reference is now made to FIG. 1, which shows a block diagram of the medical device (100). The medical device comprises an MI (110) operably coupled to an accelerometer (120). The whole MD may be movable or stationary. In some embodiments, the medical device is comprised solely from the MI. In other embodiments, the MI is physically or wirelessly connected to the medical device. The MI may also be integrated within other parts of the medical device. The medical device may further comprise a processor, other movable or stationary instruments, a cart for transporting the device, chargers, etc.

An MI can be proactive, meaning that it exerts and effect on the body it is used on or non-proactive, meaning that do not have an effect on the body but rather only collect measurements from it.

There are two types of proactive MIs. The first type includes instruments intended for deforming the patient's body in a controlled manner, for example, dental equipment like drills or surgical tools (knives, lasers). These instruments may be hazardous while they are in transit to and from their site of action as they can injure the user or the patient. When these instruments are neutralized while in motion and activated only when are minimally moving in their site of action, their hazardous potential is dramatically reduced. The second type of proactive MI's are those that introduce energy within the body of a patient. Although the radiation does not become more hazardous when the instrument is in motion, it loses, in most cases, its effect since it is not directed to a specific spot in the case of therapeutic radiation (radiotherapy, for example) or it is not able to pick a signal in the case of diagnostic radiation (ultrasound, for example). Therefore, determining the range of acceleration in which these instruments may operate by an accelerometer attached to them will dramatically reduce injuries and over exposure to radiation of patients as well as users of the instruments (mainly medical staff).

In one embodiment of the invention, the medical device is an FHRM (100) which has the same general structure. The Doppler transducer serves as the MI (210). It is defined as proactive as it emits US energy that affects the fetus and the mother. Once the transducer is moved there is no possibility of acquiring a significant signal and the US emitted is futile. If an accelerometer is attached to the Doppler transducer, it can identify three situations of movement of the instrument: (1) no movement at all, meaning the transducer is not in use. In this case, the acceleration is beneath the optimal range; (2) strong movements, meaning the transducer is in transit either it is being brought to the patient or it is moved too quickly around the abdomen of the expecting mother in search of the fetal heartbeat. In this kind of movement a signal cannot be acquired; and (3) movement within a "optimal range" in which the movement is strong enough to indicate usage (movement resulting from normal tremor of the user or breathing movements) but not too strong that signal cannot be acquired. A transducer within the optimal range is expected to have an acceleration characteristic for a transducer held by a user and placed on a specific point on the abdomen of the expectant mother.

Figure 2A:
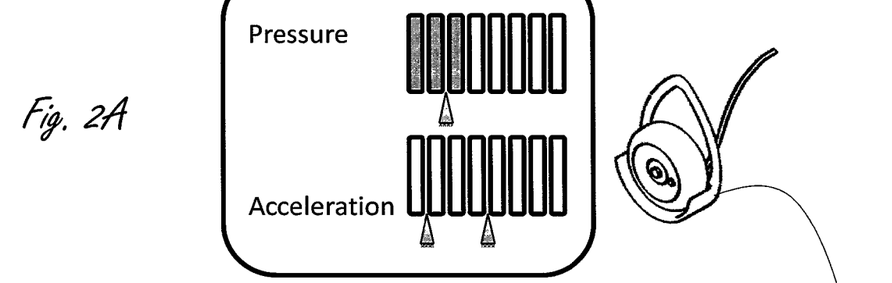
FIG. 2a illustrating in a non-in-scale manner one embodiment of the current invention in which an FHRM is in its base in an inactivated configuration (200)
Figure 2B:
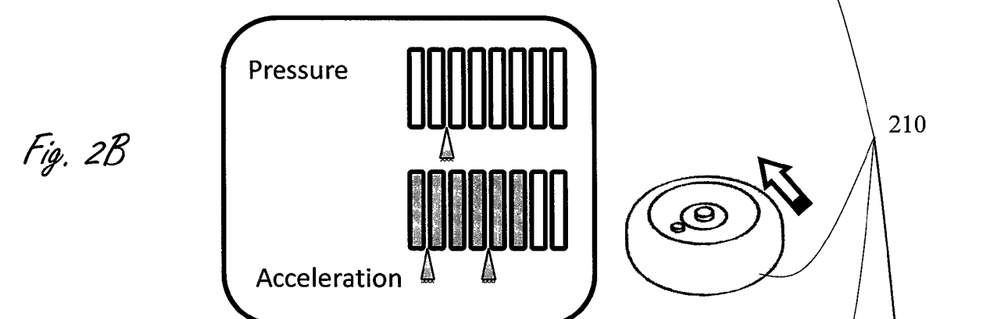
FIG. 2b illustrating in a non-in-scale manner one embodiment of the current invention in which an FHRM in transit from its base to the site of action in an inactivated configuration (200)
Figures 2C, 2D:
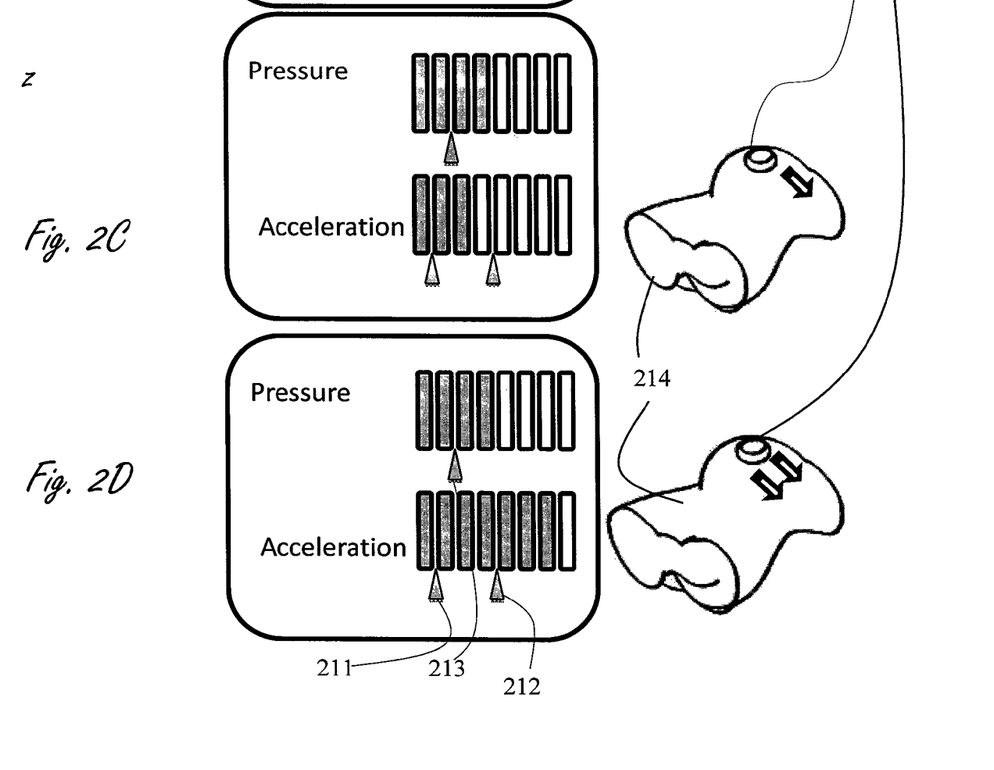
FIG. 2c illustrating in a non-in-scale manner one embodiment of the current invention in which an FHRM is in its site of action in a transceiving configuration (200)
FIG. 2d illustrating in a non-in-scale manner one embodiment of the current invention in which an FHRM is in motion on its site of action in an inactivated configuration (200)

Reference is now made to FIG. 2 which is illustrates different modes of an FHRM (210). The FHRM is adapted to be in a transceiving mode only when two conditions are met: the FHRM is within a certain range of acceleration (optimal range) (211 corresponds to the lower threshold and 212 corresponds to the upper threshold) and pressure above a certain threshold (213) is applied on the FHRM. In order to measure the acceleration an accelerometer is operably coupled to the FHRM and for pressure measurements a pressure sensor module is also coupled.

Reference is now made to FIG. 2a which is an illustration of an FHRM in its base in an inactivated configuration. When the FHRM is set in its base its acceleration is below the optimal range. The bottom threshold corresponds to the acceleration of the FHRM when it is affected solely from essential human movements. On the base there is no movement at all and therefore the acceleration is below the threshold. The pressure is above the minimal threshold since the base is applying on it pressure. As previously stated two conditions need to be met in order for the FHRM to be in its transceiving configuration and in this case only one condition is met and therefore the FHRM is in its inactivated configuration. This setting prevents the FHRM of transceiving while not in use in therefore prevents unnecessary energy waste and saves on battery in case of a battery powered FHRM.

Reference is now made to FIG. 2b which is an illustration of an FHRM in transit from its base to the site of action in its inactivated configuration. When a user decides to operate the FHRM he draws it from its base and moves it towards a living body (pregnant woman). The acceleration of this movement is above the upper threshold of the optimal range and no pressure is applied on the FHRM and therefore neither of the two conditions are met and the FHRM is in its inactive configuration. This setting prevents from the FHRM to be in a transceiving configuration while in transit and similar to FIG. 2a prevents from waste of energy and on top of it prevent from unnecessary amounts of energy to enter the user and/or the pregnant woman the FHRM is used on.

Reference is now made to FIG. 2c which is an illustration of an FHRM in its site of action in a transceiving configuration. When the FHRM is placed on the abdomen (214) of an expecting mother and it is not moving then the acceleration is within the optimal range. It is above the lower threshold (211) because it senses acceleration from the essential human movements of the mother and the user. These movements include breathing movements and other involuntarily movements. It is below the upper threshold (212) because there is no other movement of the FHRM. In addition, pressure from the abdomen is applied on the FHRM so the pressure sensed is above the minimum pressure threshold. Therefore, both conditions are met and the FHRM is in a transceiving configuration. When the FHRM is stationary on the abdomen it can receive significant signals from the fetus reflecting his heartbeat.

Reference is now made to FIG. 2d, which is an illustration of an FHRM in motion on its site of action in an inactivated configuration. When a user searches for a heartbeat signals he moves the FHRM (210) around the abdomen of the expectant mother (214). If the FHRM is moved in a low acceleration there is a chance of receiving a signal. However if the acceleration is too high there is no option for receiving a significant signal and therefore there is no point for the FHRM to be in a transceiving configuration. In this case the acceleration will be above the upper threshold (212) of the acceleration and the pressure will also be above the minimal threshold since pressure of the abdomen is applied on the FHRM. Only one condition is met and therefore the FHRM will be in its inactive configuration. This setting prevents from unnecessary amount of energy to be introduced to the mother and the fetus which may be harmful.

Another embodiments of the invention may also include an FHRM additionally operably coupled to a PPG that measures the density of the red blood cells on top of the pressure sensing module and the accelerometer. The PPG gives an indication whether the FHRM is place on a living body which gives extra assurance that the FHRM should be in its transceiving configuration.

Another embodiments of the invention may also include an FHRM or any other medical device with a movable instrument attached only to an accelerometer.

Another embodiment of the invention may also include an upper threshold of acceleration that allows transceiving while the FHRM is slowly moved on the abdomen of the expectant mother.

Figure 3:
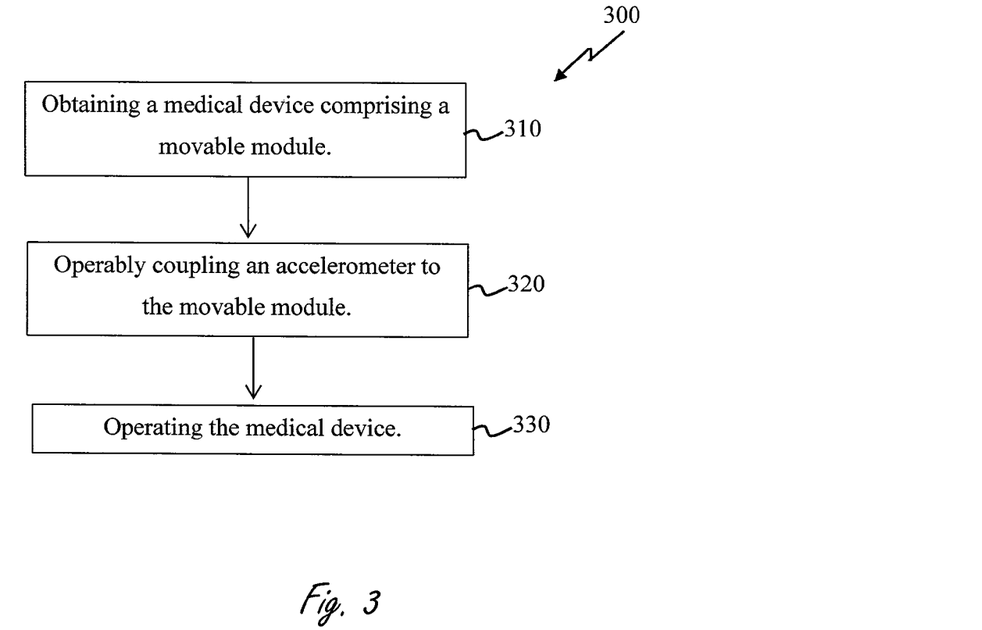
FIG. 3 is a schematic flow diagram illustrating the method for operating a medical device with a movable instrument (300); and, FIG. 4 is a schematic flow diagram illustrating the method for operating a fetal heart rate monitor with a movable Doppler transducer (400).

Reference is now made to FIG. 3, which is a schematic flow diagram illustrating the method for operating a medical device with a MI (300). In the first step, a medical device comprising a MI is obtained (310). If the medical device is intended for home use than the user may either be another person or the user can use it on himself. In the next step the MI is operably coupled to an accelerometer (320). It also possible to couple the instrument to a pressure sensor module and/or a PPG. In the case of a coupled pressure sensor, it is possible to set the instrument to function when the pressure is above a certain value that indicates that it was placed on a patient. In the case of a coupled PPG it is possible to set the instrument to function only above a certain value that indicates that the instrument was put on a living subject. In the last step, the medical device is being operated (330). The operation of the device is carried out exactly like the operation of any medical device. The only difference is that the instrument would not operate unless it is has an acceleration within the range defined.

In one embodiment of the invention there is a manual activator of the MI that needs to be activated in order for the MI to be in the active configuration. IN this embodiment the MI will be in the active configuration only when its acceleration is within the optimal range and when the manual activator is activated.

Figure 4:
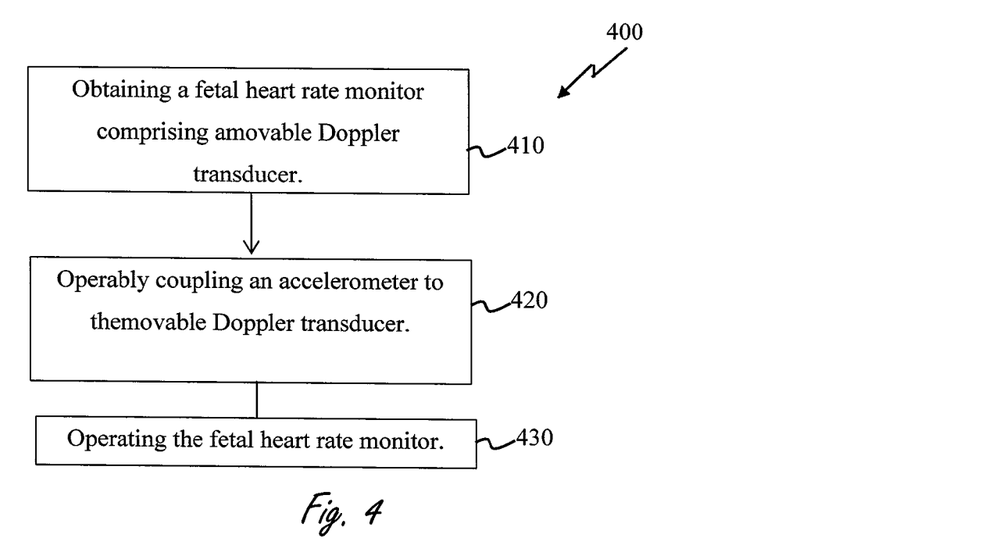

Reference is now made to FIG. 4, which is a schematic flow diagram illustrating the method for operating an FHRM with a movable Doppler transducer (400). In the first step, an FHRM comprising a Doppler transducer is obtained (410). The Doppler transducer is operably coupled to an accelerometer which determines when it is in the optimal range to emit US radiation with high chance of receiving a meaningful signal. In addition to the accelerometer, the transducer may also be coupled to a pressure sensor which will sense whether enough pressure is applied by the abdomen of the pregnant mother to receive a signal. The transducer may start transceiving only above a predetermined pressure. It is also possible to attach a PPG to the transducer that would sense whether the transducer is put on a living body.

In another embodiment the MI of a medical device, to which an accelerometer is embedded, is affixed to the body of a patient. Therefore, the MI has exactly the same acceleration as the body of the patient it is attached to and there is no movement whatsoever between the sensor and the body. The accelerometer activates and deactivates the MI according to the movement of the patient. For example, a Doppler transducer is affixed to a pregnant woman having an NST test for following the fetal heartbeat over a period of time. The Doppler transducer is embedded to an accelerometer that activates the transducer only when its acceleration is within an optimal range. Therefore, the transducer will be affected by movements of the mother. If she makes movements which are above the optimal range (like jumping, walking; depending on the upper threshold of the optimal range) the transducer will cease from emitting US energy.

The invention claimed is:
1. A fetal heart rate monitor comprising
at least one Doppler transducer configured to be placed on and moved along or around an abdomen of a pregnant woman; and
at least one accelerometer operably coupled to said at least one Doppler transducer, wherein said at least one accelerometer is configured to:
measure acceleration of said at least one Doppler transducer,
activate said at least one Doppler transducer to operate in an active configuration when the acceleration of said at least one Doppler transducer measured by said at least one accelerometer is within a predetermined range of acceleration in situ, wherein said active configuration comprises receiving and monitoring fetal heart rate signals, and
deactivate said at least one Doppler transducer to operate in an inactive configuration when said acceleration is outside said predetermined range, wherein said inactive configuration comprises not emitting energy or receiving signals;
wherein said predetermined range is bounded by a lower essential movement threshold determined for said pregnant woman and a predetermined proactive upper movement threshold;
wherein said at least one accelerometer is configured to determine said lower essential movement threshold based on base line involuntary movements of the pregnant woman measured by said at least one accelerometer while placed on the abdomen of the pregnant woman; and wherein said proactive upper movement threshold corresponds to said at least one Doppler transducer being moved by a user on the abdomen of the pregnant woman.

2. The fetal heart rate monitor of claim 1, wherein said fetal heart rate monitor further comprises a processor comprising an input module for receiving said acceleration from said at least one accelerometer and directions thereon for determining whether said acceleration is within said predetermined range according to a predefined number (n) of measurements taken in a certain period of time.

3. The fetal heart rate monitor of claim 1,
wherein said at least one Doppler transducer comprises at least one piezoelectric ceramic element configured to detect pressure by measuring electric capacity changes in the piezoelectric ceramic element; and
wherein said at least one Doppler transducer is adapted to operate in said active configuration when both (a) the pressure detected by said at least one piezoelectric ceramic element is above a predetermined threshold resulting from pressure applied when the at least one Doppler transducer is placed on the pregnant woman's body and (b) said acceleration of said at least one Doppler transducer measured by said at least one accelerometer is within said predetermined range of acceleration in situ.

4. The fetal heart rate monitor of claim 1, wherein said inactivated configuration comprises a configuration in which all functions of said fetal heart rate monitor excluding said at least one accelerometer are deactivated when said acceleration is below said lower essential movement threshold.

5. The fetal heart rate monitor of claim 1, further comprising a manual activator; wherein said manual activator and said at least accelerometer are configured to activate said at least one Doppler transducer to operate in said active configuration only when both (a) the acceleration of said at least one Doppler transducer measured by said at least one accelerometer is within said predetermined range and (b) said manual activator is activated.

6. A method for home use of a fetal heart rate monitor, said fetal heart rate monitor comprising at least one Doppler transducer and at least one accelerometer operably coupled to said at least one Doppler transducer, the method comprising:
placing said at least one Doppler transducer and said at least one accelerometer on an abdomen of a pregnant woman;
measuring base line involuntary movements of the pregnant woman in situ using said at least one accelerometer placed on the abdomen of the pregnant woman;
determining a lower essential movement threshold for the pregnant woman based on said base line involuntary movements measured by said at least one accelerometer;
measuring acceleration of said at least one Doppler transducer using said at least one accelerometer;
activating said at least one Doppler transducer to operate in an active configuration when said acceleration of said at least one Doppler transducer measured by said at least one accelerometer is within a predetermined range of acceleration in situ, wherein said active configuration comprises receiving and monitoring fetal heart rate signals, wherein said predetermined range is bounded by said lower essential movement threshold and a predetermined proactive upper movement threshold, and wherein said proactive upper movement threshold corresponds to said at least one Doppler transducer being moved by a user on the abdomen of said pregnant woman;
moving said at least one Doppler transducer from the in situ position on the abdomen of the pregnant woman; and
deactivating said at least one Doppler transducer to operate in an inactive configuration when said acceleration is outside said predetermined range, wherein said inactive configuration comprises not emitting energy or receiving signals.

7. The method of claim 6, further comprising attaching a processor to said fetal heart rate monitor; wherein said processor is configured for receiving said acceleration and has directions thereon for determining whether said acceleration is within said predetermined range according to a predefined number (n) of measurements taken in a certain period of time.

8. The method of claim 6,
wherein said at least one Doppler transducer comprises at least one piezoelectric ceramic element configured to detect pressure by measuring electric capacity changes in the piezoelectric ceramic element; and
wherein said activating said at least one Doppler transducer to operate in said active configuration comprises activating said at least one Doppler transducer to operate in said active configuration when both (a) the pressure detected by said at least one piezoelectric ceramic element is above a predetermined threshold and (b) said acceleration of said at least one Doppler transducer measured by said at least one accelerometer is within a predetermined range of acceleration in situ.

9. The method of claim 6, wherein said deactivating said at least one Doppler transducer to operate in said inactive configuration further comprises deactivating all functions of said fetal heart rate monitor, excluding said at least one accelerometer, when said acceleration is below said lower essential movement threshold.

\* \* \* \* \*